US009826937B2

(12) United States Patent
Wang et al.

(10) Patent No.: US 9,826,937 B2
(45) Date of Patent: Nov. 28, 2017

(54) METHOD AND APPARATUS FOR REDUCING MOTION ARTIFACTS IN ECG SIGNALS

(71) Applicant: KONINKLIJKE PHILIPS N.V., Eindhoven (NL)

(72) Inventors: Jin Wang, Shanghai (CN); Dan Zhao, Shanghai (CN); Cheng Shi, Shanghai (CN); Shiyang Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 141 days.

(21) Appl. No.: 14/654,570

(22) PCT Filed: Dec. 13, 2013

(86) PCT No.: PCT/IB2013/060923
§ 371 (c)(1),
(2) Date: Jun. 22, 2015

(87) PCT Pub. No.: WO2014/102653
PCT Pub. Date: Jul. 3, 2014

(65) Prior Publication Data
US 2015/0342534 A1    Dec. 3, 2015

(30) Foreign Application Priority Data

Dec. 31, 2012  (WO) ............... PCT/CN2012/087984

(51) Int. Cl.
*A61B 5/04*    (2006.01)
*A61B 5/00*    (2006.01)
*A61B 5/0452*  (2006.01)

(52) U.S. Cl.
CPC ........ *A61B 5/7207* (2013.01); *A61B 5/04017* (2013.01); *A61B 5/0452* (2013.01)

(58) Field of Classification Search
CPC ... A61B 5/5258; A61B 5/7207; A61B 5/7203; A61B 5/04017; A61B 5/0452
See application file for complete search history.

(56) References Cited

U.S. PATENT DOCUMENTS 4,732,158 A    3/1988  Sadeh
5,259,387 A   11/1993  dePinto
(Continued)

FOREIGN PATENT DOCUMENTS

EP    2319409 A1    5/2011

OTHER PUBLICATIONS

Q-Stress User Guide/Service Manual, P/N 000483-894 Rev New, 2002, 202 Page Document.

*Primary Examiner* — Michael Carey
*Assistant Examiner* — Natasha Patel

(57) ABSTRACT

The present invention provides a method and apparatus for reducing motion artifacts in ECG signals. According to an aspect of the present invention, there is proposed a method of reducing motion artifacts in ECG signals, comprising: acquiring a current beat from a continuously measured ECG signal of a patient; calculating a correlation coefficient between a previous mean value beat and the current beat in the ECG signal; determining the weights to be assigned to the previous mean value beat and the current beat based on the correlation coefficient; and calculating a current mean value beat based on the previous mean value beat, the current beat, and the weights thereof. Accordingly, the novel method of deriving the current mean value beat may reduce ECG artifacts due to patient movement in such a manner that the SNR of the ECG signal can be improved substantially.

15 Claims, 3 Drawing Sheets

(56) References Cited

U.S. PATENT DOCUMENTS

| | | |
|---|---|---|
| 5,521,851 A | 5/1996 | Wei et al. |
| 5,564,428 A | 10/1996 | Soernmo et al. |
| 5,704,365 A * | 1/1998 | Albrecht ............... A61B 5/0408 128/901 |
| 5,908,393 A | 6/1999 | Albrecht et al. |
| 6,216,031 B1 | 4/2001 | Findeis et al. |
| 6,850,796 B1 | 2/2005 | Mortara |
| 2004/0167578 A1 | 8/2004 | Warren |
| 2008/0183093 A1* | 7/2008 | Duann ............... A61B 5/04525 600/516 |
| 2010/0280402 A1 | 11/2010 | Dunbar et al. |

* cited by examiner

METHOD AND APPARATUS FOR REDUCING MOTION ARTIFACTS IN ECG SIGNALS

CROSS-REFERENCE TO PRIOR APPLICATIONS

This application is the U.S. National Phase application under 35 U.S.C. §371 of International Application No. PCT/IB2013/060923, filed on Dec. 13, 2013, which claims the benefit of Chinese Patent Application No. PCT/CN2012/087984, filed on Dec. 31, 2012. These applications are hereby incorporated by reference herein.

FIELD OF THE INVENTION

The present invention relates to a motion artifact removal technique for processing physiological signals and more particularly to a method and apparatus for reducing motion artifacts in ECG signals.

BACKGROUND OF THE INVENTION

Biological signals, for example electrocardiogram (ECG) signals, may include substantial amounts of noise. For example, noise introduced by muscular activity, motion artifacts, etc, which usually appear as rapid, wavy deflections that render the ECG difficult to read, especially during the movement.

In this regard, U.S. Pat. No. 6,216,031B1 proposes an apparatus for enhancing signals in an ECG including artifacts, which apparatus comprises a mean value unit for evaluating the curve shape of a predetermined number of ECG signal beats from the beginning of a QRS complex to the end of a T wave, and using the outcome to establish a mean value beat, and it further comprises a subtracting unit for subtracting the ECG signal's mean value beat from an actual beat to obtain a residual signal, and a FIR filter unit for high-low-pass filtering the residual signal to provide a filtered signal to which the mean value beat is added in an adding unit.

The principle of U.S. Pat. No. 6,216,031B1 is to utilize the mean value unit to calculate the mean value beat based on averaging of successive ECG cycles and utilize the LP (low pass) and HP (high pass) filters to deal with residual signals to remove both muscle noises and baseline wander noises. Although this method enhances the signal-to-noise ratio (SNR) of the resulted ECG signal to some extent, it still has some unacceptable defects.

Furthermore, in U.S. Pat. No. 6,216,031B1, normal LP/HP filtering skill is used to remove the noises. For example, the residual signal is filtered by a low-pass filter to reduce muscle noise, and by a high-pass filter to reduce baseline wander. The cutoff frequencies of the filters are set to values that avoid unacceptable distortion of the remaining P waves and VPBs in the residual signal. Both filters are finite impulse response filters with the advantage that the delay of the filtered residual signal is constant and signal-independent. But unacceptable notches may also appear, particularly in the case of an abrupt ECG morphology change.

SUMMARY OF THE INVENTION

Therefore, it would be advantageous to provide an improved method and apparatus for reducing motion artifacts in ECG signals in order to deal with unacceptable notches, and meanwhile avoid distortions and further improve the SNR of the ECG signal.

In accordance with an aspect of the present invention, there is proposed a method of reducing motion artifacts in ECG signals, comprising: acquiring a current beat from a continuously measured ECG signal of a patient; calculating a correlation coefficient between a previous mean value beat and the current beat in the ECG signal; determining the weights to be assigned to the previous mean value beat and the current beat based on the correlation coefficient; and calculating a current mean value beat based on the previous mean value beat, the current beat, and the weights thereof.

Therefore, with this method, since weight determination is based on correlation calculation, different weights can be dynamically assigned to both the previous mean value beat and the current beat according to the correlation between current beat waveform and previous mean value beat. In other words, if the correlation is high, a larger weight will be assigned to the previous mean value beat. Otherwise, it will be assigned a smaller weight, even a zero-value weight, which implies that the current beat is not correlated with the mean beat and not used for the mean beat update.

Accordingly, compared with the conventional method of calculating the mean value beat based on the previous mean value beat, the current beat and the fixed weights assigned to each of said beats, the method in accordance with the present invention adopts an adaptive weight determination method, which is based on the correlation between the two beats and which may grasp the exact ECG morphology change, resulting in an enhanced filtering effect such that the artifacts due to motion of the patient can be removed.

Here, those skilled in the art may easily understand that, in the method of enhancing signals in an ECG including artifacts, a mean value beat should be calculated or empirically determined as the initial mean value beat before the start of the real filtering of the ECG signal.

When the method of filtering of the ECG signal starts, during the processing of the first current beat, the initial mean value beat will be used as the previous mean value beat and will be combined with the first current beat to calculate the first current mean value beat, which will be stored in a memory. Then, the first current mean value beat will be subtracted from the first current beat to obtain a residual signal if these two beats are correlated, and the residual signal will be filtered to obtain a filtered signal. Finally, the filtered signal will be added back to the first current mean value beat to obtain a modified first current beat.

Next, during the processing of the second current beat, the stored first current mean value beat will be used as the previous mean value beat to be combined with the second current beat to calculate the second current mean value beat, which will be stored in a memory. Then, if the second current beat is correlated with the previous mean beat, the second current mean value beat will be subtracted from the second current beat to obtain a residual signal, and the residual signal will be filtered to obtain a filtered signal. Finally, the filtered signal will be added back to the second current mean value beat to obtain a modified second current beat. The processing operation continues like this and finally the ECG signals are all processed and filtered.

Please note that the correlation between the previous mean value beat and the current beat may be a correlation coefficient, but is not limited thereto, as will be easily understood by the person skilled in the art.

In an example of the method according to the present invention, after the correlation coefficient between a previous mean value beat and the current beat is calculated, the weights to be assigned to the previous mean value beat and the current beat may be determined empirically or by mapping with a lookup table. However, a preferred example of this method may further comprise a step of comparing the correlation coefficient with a predetermined coefficient, i.e., a predetermined correlation threshold. If the correlation coefficient is higher than the predetermined coefficient, a bigger weight will be assigned to the previous mean value beat. Otherwise, the previous mean value beat will be assigned a smaller weight or even a zero-value weight.

In an example of the method according to the present invention, the method may further comprise the steps of: subtracting the current mean value beat from the current beat to obtain a residual signal; performing piecewise filtering on the residual signal based on signal characteristics of the ECG signal to obtain a filtered signal; and adding the current mean value beat back to the filtered signal to obtain a modified current beat. In one example, the signal characteristics may be acquired from the ECG signal and may include the peak positions of P wave, QRS complex wave, and T wave, the segment intervals, and the noise envelope and the correlation information with the mean beat.

In a further example of the method, if the QRS complex wave is selected as the beat to be processed, the step of performing piecewise filtering may further comprise the sub-steps of: identifying the QRS segment and T and P segments in the ECG wave based on the signal characteristics, estimating the noise envelope based on the signal slope change, and the calculated correlation coefficient; and performing filtering on the different segments, respectively, by using different filters.

Compared with the conventional method of performing common filtering on the residual signal, the method according to the preferred example of the present invention adopts piecewise filtering of the residual signal to improve the effect of the noise reduction to enhance the SNR and to guarantee that the important features are undistorted.

Here, the term "piecewise filtering" means that, for example, if a QRS-complex wave is selected as the beat to be processed, one group of filters is used for one QRS segment and another group of filters is used for T and P segments based on the current beat signal characteristics, peak locations and interval information of the ECG morphology.

The subtraction of the current mean value beat from the current beat to obtain a residual signal is applied in the case when the current beat is correlated with the mean beat. Otherwise, the current beat can be reserved, for example, in the residual signal, and a different group of piece-wise filtering can be applied to keep the ECG features exact. In this situation, the group of piece-wise filters used for the uncorrelated beat is totally different from that used for the correlated beat. Since the calculation of the mean value beat is a key factor and may have great influence on the finally obtained ECG signal, the calculation of the initial mean value beat is particularly important. In normal practice, the initial mean value beat may be determined empirically by referring to a normal beat of ordinary people and may be previously stored.

However, in an example of the method according to the present invention, the method may further comprise a step of deriving an initial mean value beat from a predetermined number of consecutive beats in the ECG signal. Since the initial mean value beat is derived from the measurement performed on the patient himself, the accuracy of the mean value beat thus obtained may be improved.

In a further example of the method, the predetermined number of consecutive beats comprises a first predetermined number of consecutive beats and a second predetermined number of consecutive beats following the first predetermined number of consecutive beats. In the preferred example of the method, the step of deriving an initial mean value beat further comprises the sub-steps of: deriving an initial mean value beat from the first predetermined number of consecutive beats; and updating the initial mean value beat only when the correlation coefficient between a previous initial mean value beat and a current beat in the second predetermined number of consecutive beats is larger than a predetermined coefficient.

As can be seen from the above, in the preparation procedure of the method of the present invention, i.e., during calculating the initial mean value beat, the initial mean value beat is carefully validated by introducing a step of updating the initial mean value beat only if the correlation coefficient between a previous initial mean value beat and a current beat in the second predetermined number of consecutive beats is larger than a predetermined coefficient.

In other words, the conventional way of deriving an initial mean value beat from a predetermined number of consecutive beats only relates to deriving an initial mean value beat from the first predetermined number of consecutive beats by averaging or some arithmetic algorithms. However, the method according to the present invention further utilizes a second predetermined number of consecutive beats to validate and update the initial mean value beat. And the correlation coefficient between a previous initial mean value beat and a current beat in the second predetermined number of consecutive beats is also used to update the initial mean value beat.

In this way, the initial mean value beat may be derived more accurately, and accordingly the accuracy of the mean value beat thus obtained may be improved and the final filtered ECG signal may be more accurate and the SNR of the ECG signal can be further improved.

In accordance with another aspect of the present invention, there is proposed an apparatus for reducing motion artifacts in ECG signals, comprising: an acquiring unit for acquiring a current beat from a continuously measured ECG signal of a patient; a first calculating unit for calculating a correlation coefficient between a previous mean value beat and the current beat in the ECG signal; a determining unit for determining the weights to be assigned to the previous mean value beat and the current beat based on the correlation coefficient; and a second calculating unit for calculating a current mean value beat based on the previous mean value beat, the current beat, and the weights thereof.

As mentioned above, compared with the conventional apparatus for calculating the mean value beat based on the previous mean value beat, the current beat and on the fixed weights, the apparatus in accordance with the present invention adopts an adaptive weight determination method, which is based on the correlation between the two beats and may result in a good filtering effect such that the artifacts due to the motion of the patient can be removed.

Various aspects and features of the disclosure are described in further detail below. These and other aspects of the invention will be apparent from and elucidated with reference to the embodiment(s) described hereinafter.

DESCRIPTION OF THE DRAWINGS

The present invention will be described and explained hereinafter in more detail in combination with embodiments and with reference to the drawings, wherein.

Figure 1:
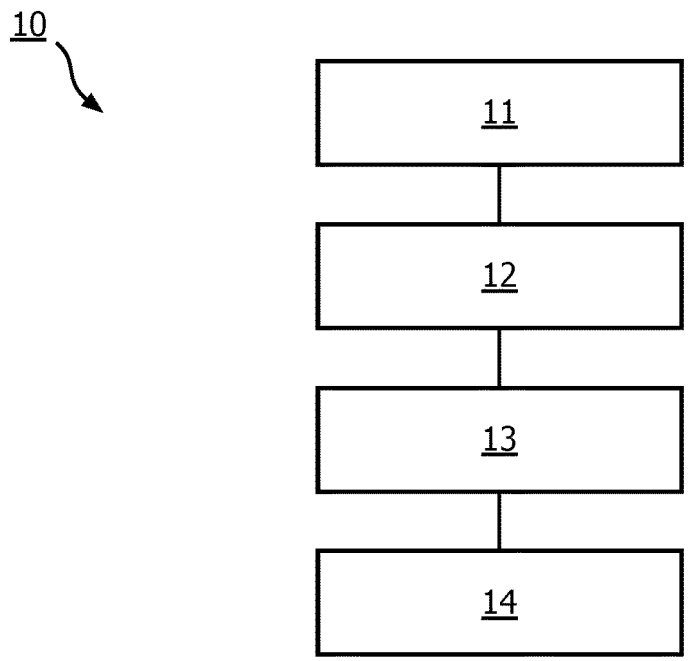
FIG. 1 is a flow chart of the method according to the invention.

The same reference signs in the figures indicate similar or corresponding features and/or functionalities.

DETAILED DESCRIPTION

The present invention will be described with respect to particular embodiments and with reference to certain drawings, but the invention is not limited thereto but is limited only by the appended claims. The drawings described are only schematic and are non-limiting. In the drawings, the size of some of the elements may be exaggerated and not drawn to scale for illustrative purposes.

FIG. 1 is a flow chart of the method 10 of reducing motion artifacts in ECG signals in accordance with one embodiment of the present invention. The method 10 as shown in FIG. 1 is directed to an improved method of calculating the current mean value beat to be used for the filtering of the current beat. Specifically, it is characterized in that it adopts an adaptive and dynamic determination of the weights to be assigned to the previous mean value beat and the current beat based on the correlation coefficient therebetween, and then the calculation of a current mean value beat is performed based on the previous mean value beat, the current beat, and the weights thereof.

In the following, details of the method 10 will be described, especially, in conjunction with FIG. 5, which is a block diagram of the apparatus 50 for implementing the method 10 shown in FIG. 1.

Figure 5:
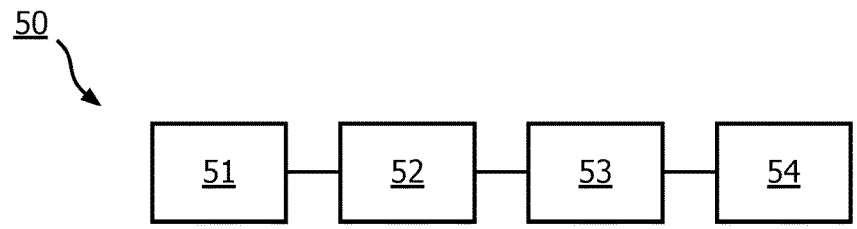
FIG. 5 is a block diagram of the apparatus according to the invention.

As can be seen from FIG. 5, the apparatus 50 for reducing motion artifacts in ECG signals in accordance with one embodiment of the present invention comprises an acquiring unit 51, a first calculating unit 52, a determining unit 53, and a second calculating unit 54.

First, an ECG sensor on a patient may continuously measure the ECG signal of the patient and the obtained ECG signal will be input to the acquiring unit 51, which may acquire a current beat from the received ECG signal (step 11 in FIG. 1).

The first calculating unit 52 is coupled with the acquiring unit 51 and is capable of calculating a correlation coefficient between a previous mean value beat and the current beat in the ECG signal (step 12 in FIG. 1).

The term "previous mean value beat" will be clearly understood by those skilled in the art based on their knowledge in this field and the detailed explanation in the present application.

As mentioned earlier, a mean value beat should be calculated or empirically determined as the initial mean value beat before the start of the real filtering of the ECG signal.

When the method of filtering of the ECG signal starts, during the filtering of the first current beat, the initial mean value beat will be used as the previous mean value beat and will be combined with the first current beat to calculate the first current mean value beat, which will be stored in a memory. Then, the first current mean value beat will be subtracted from the first current beat to obtain a residual signal if these two beats are correlated, and the residual signal will be filtered to obtain a filtered signal. Finally, the filtered signal will be added back to the first current mean value beat to obtain a modified first current beat.

Next, during the filtering the second current beat, the stored first current mean value beat will be used as the previous mean value beat to be combined with the second current beat to calculate the second current mean value beat, which will be stored in a memory. Then, if the second current beat is correlated with the mean beat, the second current mean value beat will be subtracted from the second current beat to obtain a residual signal, and the residual signal will be filtered to obtain a filtered signal. Finally, the filtered signal will be added back to the second current mean value beat to obtain a modified second current beat. The processing operation continues in this manner until finally the ECG signals are all processed and filtered.

The subtraction and addition of the mean beat from and to the current beat are applied in the situation where the current beat and the mean beat are correlated. Otherwise, the current beat may be reserved, for example in the residual signal, and then filtered to generate the output from which the noise has been removed.

Furthermore, in this method, the correlation between the previous mean value beat and the current beat may be a correlation coefficient, but is not limited thereto. For example, the correlation may be also the mean-squared value of the amplitude error or both, etc, as will be easily understood by those skilled in the art.

The determining unit 53 is coupled with the first calculating unit 52 and may determine the weights to be assigned to the previous mean value beat and the current beat based on the correlation coefficient (step 13 in FIG. 1).

For example, after the correlation coefficient between a previous mean value beat and the current beat is calculated, the weights to be assigned to the previous mean value beat and the current beat may be determined empirically or by mapping with a lookup table.

Next, the second calculating unit 54, which is coupled with the determining unit 53, is utilized for calculating a current mean value beat based on the previous mean value beat, the current beat, and the weights assigned to these beats (step 14 in FIG. 1).

Using this method 10, since the weight determination is based on correlation calculation, different weights can be dynamically assigned to both the previous mean value beat and the current beat according to the correlation between current beat waveform and previous mean value beat. In other words, if the correlation is high, a larger weight will be assigned to the previous mean value beat. Otherwise, it will be assigned a smaller weight or even a zero-value weight.

Accordingly, compared with the conventional method of calculating the mean value beat based on the previous mean value beat, the current beat and the fixed weights, the method 10 in accordance with the present invention adopts an adaptive weight determination method, which is based on the correlation between the two beats and which may result in good tracking of the ECG morphology change and in a better filtering effect, such that the artifacts due to patient motion can be removed.

Figure 2:
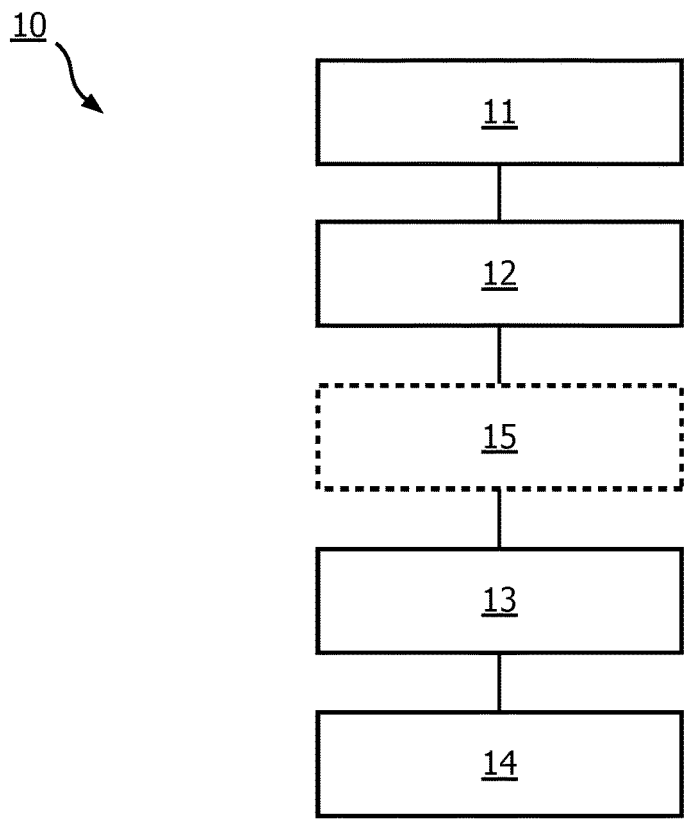
FIG. 2 shows a flow chart of a variation of the method according to the invention.
Figure 3:
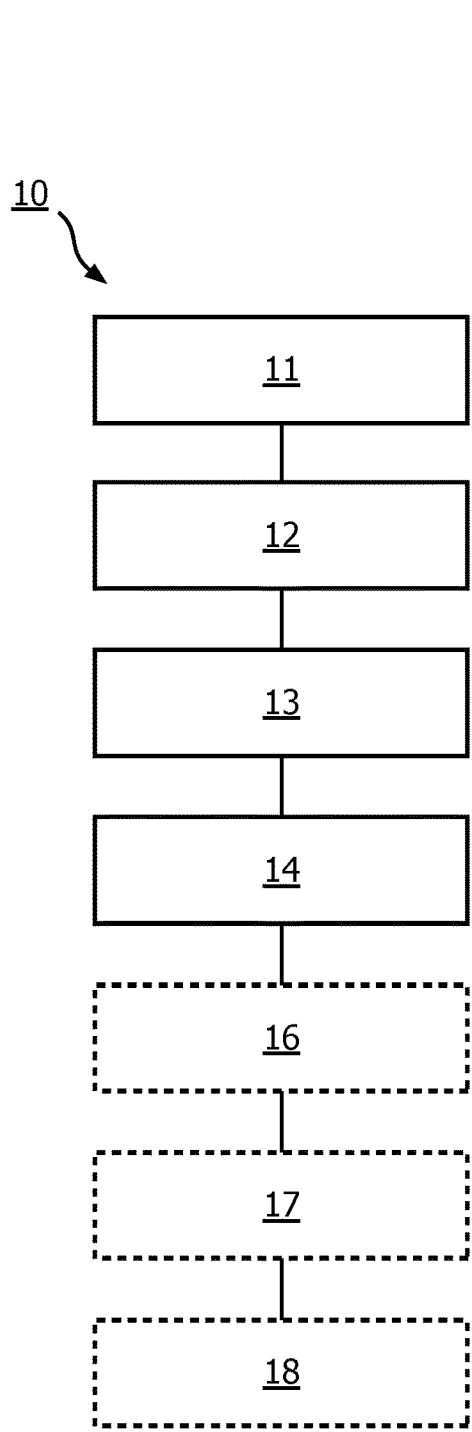
FIG. 3 shows a flow chart of another variation of the method according to the invention.
Figure 4:
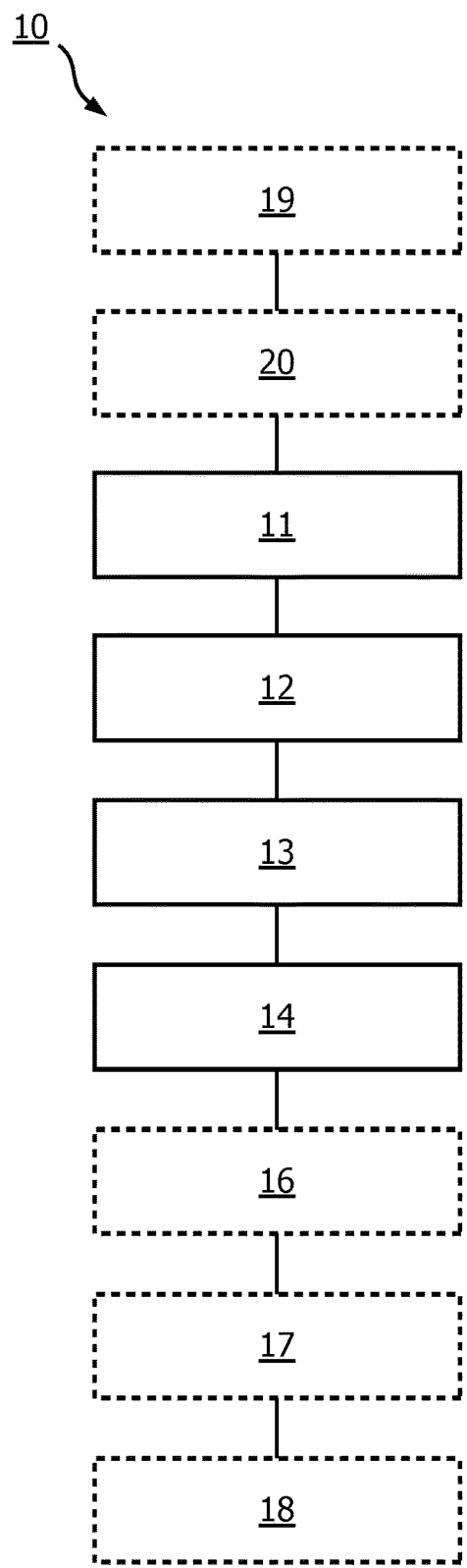
FIG. 4 shows a flow chart of still another variation of the method according to the invention.

FIGS. 2-4 show some possible variations to the method 10 of reducing motion artifacts in ECG signals in accordance with the present invention.

As shown in FIG. 2, in the preferred example of this method, the method may further comprise a step 15 of comparing the correlation coefficient with a predetermined coefficient, i.e., a predetermined correlation threshold.

For example, a correlation coefficient CCR is calculated by the correlation calculation unit and compared with a pre-determined correlation threshold, indicating whether the current cycle is highly correlated with the existing mean cycle:

$$\begin{cases} \max(CCR) > \text{threshold} & \text{highly correlated} \\ \text{otherwise} & \text{not highly correlated} \end{cases}$$

If the correlation coefficient is higher than the predetermined coefficient, a larger weight will be assigned to the previous mean value beat. Otherwise the previous mean value beat will be assigned a smaller weight or even a zero-value weight.

FIG. 3 shows a flow chart of the method 10 of reducing motion artifacts in ECG signals in accordance with a further embodiment of the present invention.

As shown in FIG. 3, in the preferred example of this method 10, the method may further comprise a step 16 of subtracting the current mean value beat from the current beat to obtain a residual signal, after the current mean value beat has been calculated based on the previous mean value beat, the current beat, and the weights thereof. When the current beat is not correlated with the mean beat, step 16 of subtraction is not applied and the beat is reserved, for example, in the residual signal directly.

Furthermore, the method 10 further comprises a step 17 of performing piecewise filtering on the residual signal based on signal characteristics of the ECG signal to obtain a filtered signal. And after step 17, the method may further comprise a step 18 in which the current mean value beat is added back to the filtered signal to obtain a modified current beat when the beat is correlated with the mean beat. Otherwise, said adding step is omitted. In this way, the current mean value beat obtained in the method 10 shown in FIG. 1 is utilized in the real filtering of the ECG signal to finally achieve that motion artifacts are removed from the ECG signal.

In one example, the signal characteristics may be acquired from the ECG signal and may include the peak positions of P wave, QRS complex wave, and T wave, and the segment intervals.

In a further example of the method 10, if the QRS complex wave is selected as the beat to be processed, step 17 of performing piecewise filtering may further comprise the sub-steps of identifying the QRS segment and T and P wave segments, the noise envelope based on the signal characteristics, and the correlation with the mean beat; and performing filtering on the different segments, respectively, by using different filters.

Compared with the conventional method of performing common filtering on the residual signal, the method 10 according to the preferred example of the present invention shown in FIG. 3 adopts piecewise filtering of the residual signal to enhance the ECG's SNR and to make sure that the ECG features remain undistorted in the motion artifact-removed signal.

Here, the term "piecewise filtering" means that, for example, if a QRS complex wave is selected as the beat to be processed, one group of LP and HP filters is used for one QRS segment and another group of LP and HP filters is used for T and P segments based on the current beat signal characteristics i.e., peak locations, interval information, the noise envelopment of the ECG morphology and the correlation information with the mean beat. In accordance with one example of the method 10 as shown in FIG. 3, the first group of low-pass filters and high-pass filters for the QRS segment and a second group of low-pass filters and high-pass filters for other segments may be different in cutoff frequency. However, as can be easily understood by those skilled in the art, the two groups of filters may be different in other parameters, as long as they are specifically selected in accordance with the signal characteristics.

In this way, piecewise LP/HP filtering based on beat characteristics can be used to deal with the notches due to the abrupt change between QRS transitions, and accordingly, the SNR of the ECG signal can be improved substantially. Moreover, at the same time, important ECG features can be perfectly maintained.

For example, a zero-phase forward and reverse low-pass filter with 20 Hz, 40 Hz, or 60 Hz cutoff frequency may be used with the following difference function:

$$y(n)=b(1)x(n)+b(2)x(n-1)+ \ldots +b(n_b)x(n-(n_b-1))-a(2)y(n-1)- \ldots -a(n_a)y(n-(n_a-1))$$

where $b(i)$, $a(j)$, $i=1 \ldots n_b$, $j=1 \ldots n_a$ are the filter coefficients.

The high-pass filter is implemented by a FIR filter with the following difference function; the order of N is selected to be N=1000. A different order value N can be selected to realize a different cutoff frequency, according to the different filtering requirements.

$$y_{n-\frac{N}{2}} = x_{n-\frac{N}{2}} - \frac{x_n + x_{n-1} + \ldots + x_{n-N+1}}{N}$$

Due to the structure of the proposed high-pass filter, a constant delay of $$\frac{N-1}{2}$$

is introduced to the piecewise filtered signal; therefore, in order to obtain the correct artifact-removed signal, when adding the mean value beats back to the filtered signal, the constant delay should be considered to compensate for the positions of the adding operations. In order to reduce the delay involved in the filtering process, a different type of HP filter may be utilized, for example, a butterworth filter with a flat pass-band.

Although the above shows some examples of the filters to be used in the method and the apparatus of the present invention, it may be easily understood by those skilled in the art that other filters with different filter coefficients and different cutoff frequency may also be used according to the specific application.

FIG. 4 shows a flow chart of the method 10 of reducing motion artifacts in ECG signals in accordance with still another embodiment of the present invention. The only difference between the methods 10 shown in FIG. 3 and FIG. 4 is that in FIG. 4 it further comprises a step 19 of acquiring, from the ECG signal, the signal characteristics, and a step 20 of selecting one of P wave, QRS complex wave, and T wave, or any combination thereof as the beat to be processed.

In this way, a raw ECG signal is processed to get signal characteristics, such as QRS positions and segment intervals, as mentioned above. Then, the related signal characteristics may be sent to a current signal template unit for classifying current signal templates. A different scheme of multiple signal templates (QRS template, T template and QRST template) may be utilized to improve the tracing of the motion artifact-removed ECG signals, which results in more accurate feature extraction for ECG diagnosis. The templates have predetermined lengths, with the central and most visually obvious parts of the tracing as the reference portions for alignment in these templates. Although signal intervals of the incoming ECG signals vary, the proposed multiple templates, and the previously discussed dynamic determined weights, ensure that the ECG signal is perfectly tracked by the updated mean value beat templates.

As mentioned earlier, a mean value beat should be calculated or empirically determined as the initial mean value beat before the start of the real filtering of the ECG signal.

Since the calculation of the mean value beat is a key factor and may have great influence on the final ECG signal obtained, the calculation of the initial mean value beat is particularly important. In normal practice, the initial mean value beat may be determined empirically by referring to a normal beat of ordinary people.

However, in a preferred example of the method 10 according to the present invention, the method may further comprise a step of deriving an initial mean value beat from a predetermined number of consecutive beats in the ECG signal. Since the initial mean value beat is derived from a measurement on the patient himself, the accuracy of the mean value beat thus obtained may be improved.

In a further preferred example of the method, the predetermined number of consecutive beats may comprise two portions, i.e., a first predetermined number of consecutive beats and a second predetermined number of consecutive beats following the first predetermined number of consecutive beats. Accordingly, in the preferred example of the method, the step of deriving an initial mean value beat may further comprise the sub-steps of deriving an initial mean value beat from the first predetermined number of consecutive beats; and updating the initial mean value beat only when the correlation coefficient between a previous initial mean value beat and a current beat in the second predetermined number of consecutive beats is larger than a predetermined coefficient.

As can be seen from the above, in the preparation procedure of the method of the present invention, i.e., during calculating the initial mean value beat, the initial mean value beat is carefully validated by introducing a step of updating the initial mean value beat only when the correlation coefficient between a previous initial mean value beat and a current beat in the second predetermined number of consecutive beats is larger than a predetermined coefficient.

In other words, the conventional way of deriving an initial mean value beat from a predetermined number of consecutive beats only relates to deriving an initial mean value beat from the first predetermined number of consecutive beats by averaging or some arithmetic algorithms. However, the method 10 according to the present invention further utilizes a second predetermined number of consecutive beats to validate and update the initial mean value beat. Here, the correlation coefficient between a previous initial mean value beat and a current beat in the second predetermined number of consecutive beats is also used to update the initial mean value beat.

In this way, the initial mean value beat may be derived more accurately, and accordingly the accuracy of the mean value beat thus obtained may be improved and the final filtered ECG signal may be more accurate and the SNR of the ECG signal can be further improved.

Furthermore, in accordance with a preferred example of the method 10 of the present invention, the method may further comprise, if necessary, a step of reactivating the step of deriving an initial mean value beat from a predetermined number of consecutive beats in the ECG signal. In other words, if the filtered ECG signal is degraded heavily and the SNR thereof is not good anymore, the user of the apparatus 50 may operate a button or the like to reactivate the step of deriving an initial mean value beat, so that a new filtering step of the ECG signal will start. In this way, the filtered ECG signal will be timely corrected.

Figure 6:
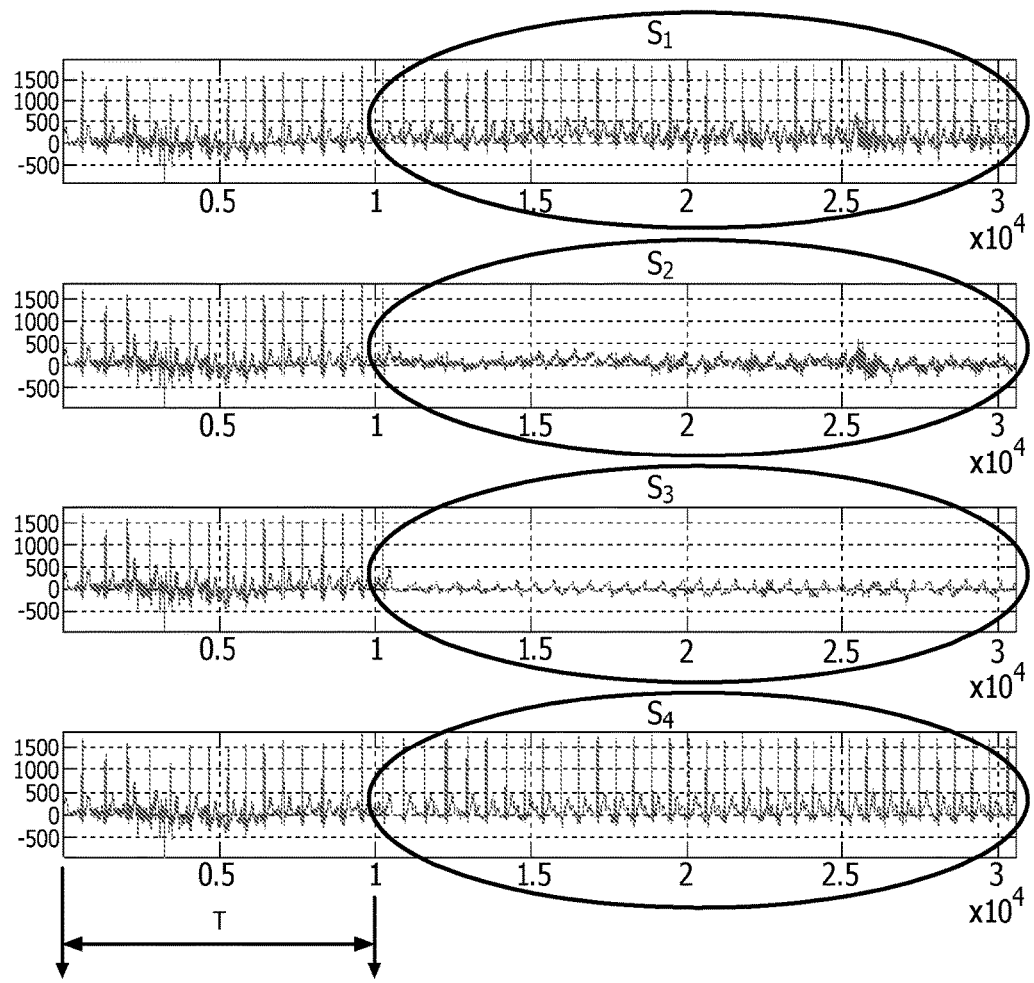
FIG. 6 shows how motion artifacts are removed from an ECG signal by utilizing the method of the invention.

FIG. 6 shows how motion artifacts are removed from ECG signals by utilizing the method of the invention.

As shown in FIG. 6, S1 represents the original or raw ECG signal received from the patient, S2 represents a residual signal obtained by subtracting the current mean value beat from the current beat, S3 represents the filtered residual signal which has been subject to piecewise filtering based on signal characteristics of the ECG signal, and S4 represents the modified current beat (i.e. the motion artifact-removed signal) by adding the current mean value beat back to the filtered signal. Furthermore, the period T shown in FIG. 6 stands for the period during which the initial mean value beat is derived from a predetermined number of consecutive beats in the ECG signal.

It is clearly shown in FIG. 6 that by means of the method 10 of the present invention, ECG artifacts due to patient movement are reduced and hence the SNR of the ECG signals is improved substantially.

Although FIG. 5 only shows a basic block diagram of the apparatus 50 according to the present invention, it may be easily understood by those skilled in the art that, there could be a unit corresponding to each step in the above described methods 10, including the steps shown in FIGS. 2-4, to perform the relevant method step. For example, in accordance with the method 10 shown in FIG. 2, the apparatus 50 according to the present invention may further comprise a comparator for comparing the correlation coefficient with a predetermined coefficient. For example, in accordance with the method 10 shown in FIG. 3, the apparatus 50 according to the present invention may further comprise a subtracting unit for subtracting the current mean value beat from the current beat to obtain a residual signal; a filter unit for performing piecewise filtering on the residual signal based on signal characteristics of the ECG signal to obtain a filtered signal; and an adding unit for adding the filtered signal back to the current mean value beat to obtain a modified current beat.

As for the units comprised in the apparatus 50, in one example, the apparatus 50 per se may be a personal computer with a CPU and a memory, a Single-chip Microcomputer or a CPU (i.e., a processing unit) alone. Therefore, the respective units comprised therein may be implemented as software or computer-readable instructions.

However, as will be easily understood by those skilled in the art, the respective units may be hardware entities as well. In other words, the apparatus 50 may be composed of distinct hardware modules. Each of the units may be implemented by a single processor or a plurality of processors.

Please note that the steps of the methods shown in the present invention should not be limited to the steps mentioned above. It will be apparent to those skilled in the art that the various aspects of the invention claimed may be practiced in other examples that depart from these specific details.

Furthermore, as can be easily understood by those skilled in the art, in the apparatus claim enumerating several means, several of these means can be embodied by one and the same item of hardware. The mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method of reducing motion artifacts in ECG signals, comprising:
   acquiring, via an acquiring unit, a current beat from a continuously measured ECG signal of a patient;
   calculating, via a first calculating unit, a correlation coefficient between a previous mean value beat and the current beat in the ECG signal;
   determining, via a determining unit, weights to be assigned to the previous mean value beat and the current beat based on the correlation coefficient; and
   calculating, via a second calculating unit, a current mean value beat based on (i) the previous mean value beat, (ii) the current beat, and (iii) the determined weights respectively assigned to the previous mean value beat and the current beat, wherein the current mean value beat comprises a motion artifact reduced beat having reduced motion artifacts over the current beat in the ECG signal.

2. The method according to claim 1, further comprising a step of comparing, via a comparator, the correlation coefficient with a predetermined coefficient.

3. The method according to claim 1, further comprising:
   subtracting, via a subtracting unit, the current mean value beat from the current beat to obtain a residual signal;
   performing, via a filter unit, piecewise filtering on the residual signal based on signal characteristics of the ECG signal to obtain a filtered signal; and
   adding, via an adding unit, the filtered signal back to the current mean value beat to obtain a modified current beat.

4. The method according to claim 3, further comprising:
   extracting, via an extracting unit, from the ECG signal, the signal characteristics, wherein the signal characteristics include (i) a noise envelope, (ii) correlation information, (iii) peak positions of P wave, QRS complex wave, and T wave, and (iv) segment intervals, and
   selecting, via a selection unit, (i) one of P wave, QRS complex wave, and T wave, or (ii) any combination thereof, as the current beat to be processed.

5. The method according to claim 4, wherein, responsive to selecting the QRS complex wave as the current beat to be processed, the step of performing piecewise filtering further comprises the sub-steps of:
   identifying, via an identification unit, a QRS segment and T and P segments based on the signal characteristics; and
   performing filtering on the QRS, T and P segments, respectively, via different filters.

6. The method according to claim 1, further comprising deriving, via a derivation unit, an initial mean value beat from a predetermined number of consecutive beats in the ECG signal.

7. The method according to claim 6, wherein the predetermined number of consecutive beats comprises (i) first predetermined number of consecutive beats and (ii) a second predetermined number of consecutive beats following the first predetermined number of consecutive beats, and wherein the step of deriving an initial mean value beat further comprises the sub-steps of:
   deriving an initial mean value beat from the first predetermined number of consecutive beats; and
   updating the initial mean value beat only in response to the correlation coefficient between a previous initial mean value beat and a current beat in the second predetermined number of consecutive beats being larger than a predetermined coefficient.

8. The method according to claim 6, further comprising:
   reactivating, in response to a user operation of a reactivation button, the step of deriving an initial mean value beat from a predetermined number of consecutive beats in the ECG signal.

9. The method according to claim 1, wherein the steps of acquiring via the acquiring unit, calculating via the first calculating unit, determining via the determining unit, and calculating via the second calculating unit are applied to single channel ECG signals.

10. An apparatus for reducing motion artifacts in ECG signals, comprising:
    an acquiring unit for acquiring a current beat from a continuously measured ECG signal of a patient;
    a first calculating unit for calculating a correlation coefficient between a previous mean value beat and the current beat in the ECG signal;
    a determining unit for determining the weights to be assigned to the previous mean value beat and the current beat based on the correlation coefficient; and
    a second calculating unit for calculating a current mean value beat based on (i) the previous mean value beat, (ii) the current beat, and (iii) the determined weights respectively assigned to the previous mean value beat and the current beat, wherein the current mean value beat comprises a motion artifact reduced beat having reduced motion artifacts over the current beat in the ECG signal.

11. The apparatus according to claim 10, further comprising a comparator for comparing the correlation coefficient with a predetermined coefficient.

12. The apparatus according to claim 10, further comprising:
    a subtracting unit for subtracting the current mean value beat from the current beat to obtain a residual signal;
    a filter unit for performing piecewise filtering on the residual signal based on signal characteristics of the ECG signal to obtain a filtered signal; and
    an adding unit for adding the filtered signal back to the current mean value beat to obtain a modified current beat.

13. The apparatus according to claim 12, further comprising:
    an extracting unit for extracting, from the ECG signal, the signal characteristics, wherein the signal characteristics include (i) a noise envelope, (ii) correlation information, (iii) peak positions of P wave, QRS complex wave, and T wave, and (iv) segment intervals; and a selection unit for selecting (i) one of P wave, QRS complex wave, and T wave, or (ii) any combination thereof, as the current beat to be processed.

14. The apparatus according to claim 13, wherein responsive to the selection unit selecting the QRS complex wave as the current beat to be processed, the apparatus further comprising:

an identifying unit for identifying a QRS segment and T and P segments based on the signal characteristics, and wherein the filtering unit comprises a first group of low-pass filters and high-pass filters for the QRS segment and a second group of low-pass filters and high-pass filters for T and P segments, respectively.

15. The apparatus according to claim 14, wherein the first group of low-pass filters and high-pass filters for the QRS segment and the second group of low-pass filters and high-pass filters are different in cutoff frequency.

* * * * *